United States Patent
Urushiyama et al.

(10) Patent No.: US 9,507,029 B2
(45) Date of Patent: Nov. 29, 2016

(54) SILVER-CONTAINING LITHIUM HEPTABORATE PHOTOSTIMULABLE PHOSPHOR, METHOD FOR PRODUCING SAME, AND LAMINATE USING SAID PHOTOSTIMULABLE PHOSPHOR

(75) Inventors: Akio Urushiyama, Tokyo (JP); Chie Kurokawa, Tokyo (JP)

(73) Assignees: Rikkyo Gakuin, Tokyo (JP); JUNTENDO EDUCATIONAL FOUNDATION, Tokyo (JP)

( * ) Notice: Subject to any disclaimer, the term of this patent is extended or adjusted under 35 U.S.C. 154(b) by 576 days.

(21) Appl. No.: 14/008,688

(22) PCT Filed: Mar. 14, 2012

(86) PCT No.: PCT/JP2012/057254
§ 371 (c)(1),
(2), (4) Date: Sep. 30, 2013

(87) PCT Pub. No.: WO2012/133070
PCT Pub. Date: Oct. 4, 2012

(65) Prior Publication Data
US 2014/0023842 A1   Jan. 23, 2014

(30) Foreign Application Priority Data

Mar. 31, 2011   (JP) ................................ 2011-077556
Oct. 7, 2011   (JP) ................................ 2011-223026

(51) Int. Cl.
| | |
|---|---|
| *C09K 11/08* | (2006.01) |
| *C09K 11/63* | (2006.01) |
| *G01T 1/00* | (2006.01) |
| *G01T 1/11* | (2006.01) |
| *G21K 4/00* | (2006.01) |
| *C09K 11/58* | (2006.01) |
| *A61N 5/10* | (2006.01) |
| *C09K 11/02* | (2006.01) |

(52) U.S. Cl.
CPC .............. *G01T 1/11* (2013.01); *A61N 5/1071* (2013.01); *C09K 11/025* (2013.01); *C09K 11/586* (2013.01); *C09K 11/63* (2013.01); *Y10T 428/24967* (2015.01); *Y10T 428/269* (2015.01)

(58) Field of Classification Search
CPC ........ C09K 11/58; C09K 11/025; G01T 1/11
See application file for complete search history.

(56) References Cited

U.S. PATENT DOCUMENTS

| | | | |
|---|---|---|---|
| 4,248,731 A | 2/1981 | Takenaga et al. | |
| 2013/0161560 A1* | 6/2013 | Urushiyama | C09K 11/634 252/301.4 R |

FOREIGN PATENT DOCUMENTS

WO   WO 2012/029951 A1 *   3/2012

OTHER PUBLICATIONS

Extended European Search Report in EP 12 76 3350 dated Aug. 7, 2014.
International Search Report for PCT/JP2012/057254, mailed May 29, 2012.
Ozdemir et al, "Investigation of Thermoluminescence Properties of Metal Oxide Doped Lithium Triborate", J. Mater. Sci. (2007) 42:8501-8508.
Sastry et al, "Studies in Lithium Oxide Systems: I, $Li_2O$ $B_2O_3$—$B_2O_3$", Journal of the American Ceramic Society, vol. 41, 7-17 (1958).

* cited by examiner

*Primary Examiner* — Carol M Koslow
(74) *Attorney, Agent, or Firm* — Nixon & Vanderhye P.C.

(57) ABSTRACT

The present invention aims to provide a photostimulable phosphor for obtaining a two-dimensional or three-dimensional dosimeter, the photostimulable phosphor exerting superior handleability, exhibiting superior biological equivalence, and having superior precision. The present invention also aims to provide a laminate using the photostimulable phosphor.

The aforementioned objects are achieved by means of a method for producing a photostimulable phosphor, the method comprising a step A for mixing lithium tetraborate, boron oxide and silver oxide and a step B for obtaining the photostimulable phosphor comprising lithium heptaborate as a base material and silver as a luminescent center present in the base material by firing the aforementioned mixture at 820 to 860° C., wherein the molar ratio between the lithium tetraborate and the boron oxide in the step A is X:1 (X>1), and the amount of the silver oxide is 0.06 to 1.0 mass % relative to the total mass of the lithium tetraborate and the boron oxide.

12 Claims, 19 Drawing Sheets

Measurement after irradiation with CuKα X rays and subsequent photoexcitation with blue light-emitting diode (470 nm).
Microline cooled CCD camera (Finger Lakes Instrumentation) and U-340 ultraviolet transmission filter (HOYA) were used.

Measurement after irradiation with CuKα rays and subsequent photoexcitation with blue light-emitting diode (470 nm, 140 mW)

Ocean Optics USB2000 type spectrometer (10-second exposure) and U-340 ultraviolet transmission short pass filter were used.

Measurement after irradiation with X rays (6 MV) using Elekta linear accelerator and subsequent photoexcitation with blue light-emitting diode (470 nm)

Microline cooled CCD camera (Finger Lakes Instrumentation) and U-340 ultraviolet transmission filter were used.

Measurement after leaving to stand in dark place (0°C) and subsequent photoexcitation with blue light-emitting diode (470 nm)

Microline cooled CCD camera (Finger Lakes Instrumentation) and U-340 ultraviolet transmission filter (HOYA) were used.

Measurement after irradiation with CuKα X rays and subsequent photoexcitation with blue light-emitting diode (470 nm)

Microline cooled CCD camera (Finger Lakes Instrumentation) and U-340 ultraviolet transmission filter (HOYA) were used.

Elapsed time (sec) (see Figure 2)

Logarithmic value of attenuated luminescence intensity

Measurement after irradiation with CuKα X rays and subsequent photoexcitation with blue light-emitting diode (470 nm)

Microline cooled CCD camera (Finger Lakes Instrumentation) and U-340 ultraviolet transmission filter (HOYA) were used.

Product fired for 6 hours

Measurement after irradiation with CuKα X rays and subsequent photoexcitation with blue light-emitting diode (470 nm)

Note: Relative luminescence intensity, 51820, was observed after firing at 860°C.

Product fired for 6 hours

RIGAKU RINT diffractometer was used.

Concentration of silver oxide (mass %)

Concentration of silver oxide (mass %)

Image of luminescence corresponding to each dose (6 MV X rays)

(Each number in the lower line indicates relative luminescence intensity.)

Curve of sensitivity to X rays (6 MV)

(6 MV, Irradiation field 10 × 10 cm)

Off-center ratio (6 MV X rays, Irradiation field 10 × 10 cm, 100 mm deep)

Percentage depth dose (6 MV X rays, Irradiation field 10 × 10 cm)

Curve of sensitivity to electron beams (9 MeV)

Off-center ratio (9 MeV electron beams, Irradiation field 100 × 100 mm, 12 mm deep)

Percentage depth dose (9 MeV electron beams)

SILVER-CONTAINING LITHIUM HEPTABORATE PHOTOSTIMULABLE PHOSPHOR, METHOD FOR PRODUCING SAME, AND LAMINATE USING SAID PHOTOSTIMULABLE PHOSPHOR

This application is the U.S. national phase of International Application No. PCT/JP2012/057254 filed 14 Mar. 2012 which designated the U.S. and claims priority to JP Patent Application No. 2011-077556 filed 31 Mar. 2011 and JP Patent Application No. 2011-223026 filed 7 Oct. 2011, the entire contents of each of which are hereby incorporated by reference.

TECHNICAL FIELD

The present invention relates to a silver-containing lithium heptaborate photostimulable phosphor and a method for producing the same.

BACKGROUND ART

Today, radiation therapies for cancers are rapidly developing centering around various irradiation methods, and along with the development, the importance of measurement of three-dimensional absorbed dose is increasing. To evaluate radiation absorbed by the living body, it is necessary to use a dosimeter sensor having the same effective atomic number as that of biological tissues. Dose measured with a sensor having a different effective atomic number cannot be used to measure dose absorbed by biological tissues accurately.

A two-dimensional dose distribution is now obtained by Gafchromic film or imaging plate (IP) photoreceptor. However, since Gafchromic film can be used only once, in-plane sensitivity coefficient cannot be obtained, nor can disrupted images resulting from uneven coating of photoreceptors be corrected; hence, Gafchromic film has problems in quantitative capability. Further, Gafchromic film has a small dynamic range and this problem imposes many restrictions on use of the film. Meanwhile, since IPs are not biological tissue equivalent, it is virtually impossible to apply IPs to three-dimensional measurement. A method of measuring three-dimensional dose distribution using a molded product of a polymer gel in which a biological tissue-equivalent fluorescent substance is dispersed is also being studied, but the method is highly burdensome in terms of facilities and labor and is not practical.

Known phosphors that can be used for measurement of radiation dose are thermoluminescent phosphors, which emit light by heating after irradiation with radiation (for example, Non-patent Document 1) and photostimulable phosphors, which emit light by light irradiation after irradiation with radiation. Patent Document 1 discloses a sheet-like two-dimensional dosimeter obtained by mixing a lithium fluoride-based thermoluminescent phosphor and a binder and hot-pressing the mixture in a die. Lithium fluoride loses thermoluminescence when it is exposed to a high temperature; hence, a conventional problem is that when a lithium fluoride-based thermoluminescent phosphor is mixed with a binder and the mixture is heated and processed into a sheet, the thermoluminescence decreases. In this regard, in the invention disclosed in Patent Document 1, it is stated that the foregoing problem has been resolved since a tetrafluoroethylene-ethylene copolymer is used as a binder which is cured by heating at a relatively low temperature of 260° C. However, the effective atomic number of a lithium fluoride thermoluminescent phosphor is 8.2, which differs from the effective atomic number of biological tissues, 7.4, for photoelectric effect. Since the total effective atomic number of a sheet comprising a fluorine resin used as a binder is larger, the biological tissue equivalence of the sheet is not satisfactory.

On the other hand, a dosimeter using a photostimulable phosphor is superior in rapidity and hence, there is a demand for a photostimulable phosphor for obtaining a two-dimensional or three-dimensional dosimeter that is superior in handleability, biological tissue equivalence and precision. Non-patent Document 2 discloses that the phase transition temperature of lithium heptaborate and lithium tetraborate+liquid phase is 856±2° C. in a mixed component phase of a lithium oxide and a boron oxide (3:1). However, the document does not refer to a silver-containing lithium heptaborate photostimulable phosphor.

CITATION LIST

Patent Document

Patent Document 1: JP 2004-317136 A

Non-Patent Documents

Non-patent Document 1: Zeynep Ozdemir, Jemir, Gulhan Ozbayoglu, and Aysen Yilmaz, J. Mater Sci (2007) 42, 8501-8508

Non-patent Document 2: B. S. R. Sastry and F. A. Hummel, Journal of the American Ceramic Society, Vol. 41, 7-17 (1958)

SUMMARY OF INVENTION

Technical Problem

As mentioned above, there is a demand for a photostimulable phosphor for obtaining a two-dimensional or three-dimensional dosimeter which is superior in handleability, biological tissue equivalence and precision and which is used to measure dose absorbed by biological tissues. However, no satisfactory photostimulable phosphor has been available. In consideration of the foregoing, the present invention aims to provide a photostimulable phosphor for obtaining a two-dimensional or three-dimensional dosimeter which is superior in handleability, biological tissue equivalence and precision and which is used to measure dose absorbed by biological tissues and to provide a laminate using the photostimulable phosphor.

Solution to Problem

As a result of studies, the present inventors found that the aforementioned objects can be achieved by producing a silver-containing lithium heptaborate in accordance with a certain method, and this finding led to the completion of the present invention. More specifically, the aforementioned objects are achieved by the following inventions.

A method for producing a photostimulable phosphor, comprising a step A for mixing lithium tetraborate, boron oxide and silver oxide and a step B for obtaining the photostimulable phosphor comprising lithium heptaborate as a base material and silver as a luminescent center present in the base material by firing the above-mentioned mixture at 820 to 860° C., wherein the molar ratio between the lithium tetraborate and the boron oxide in the step A is X:1, provided that X>1, and the amount of the silver oxide is 0.06 to 1.0 mass relative to the total mass of the lithium tetraborate and the boron oxide.

A thin film body comprising paper or a biological tissue-equivalent plastic sheet and a photostimulable phosphor sheet laminated thereon which comprises lithium heptaborate as a base material and silver as a luminescent center present in the base material.

A laminate comprising a biological tissue-equivalent plastic plate and a thin film body according to (2) which is laminated on the plate.

Advantageous Effects of Invention

The present invention can provide a photostimulable phosphor for obtaining a two-dimensional or three-dimensional dosimeter that is superior in handleability, biological tissue equivalence and precision, and the invention can also provide a laminate using the photostimulable phosphor.

DESCRIPTION OF EMBODIMENTS

Figure 1:
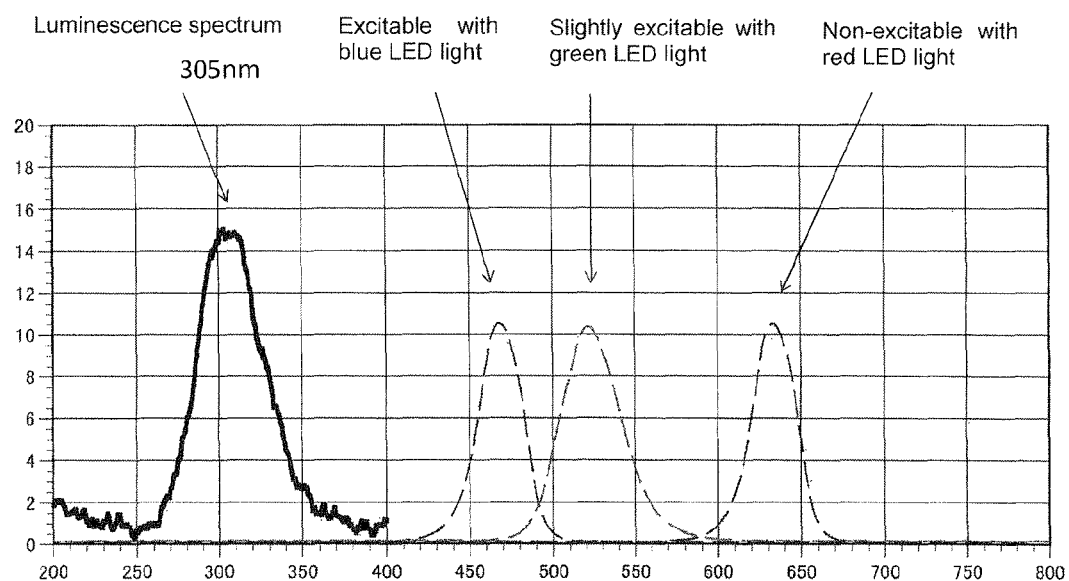
FIG. 1 shows luminescence spectra of a silver-containing lithium heptaborate.

The present invention will be described in detail below. As used herein, "A to B" means values ranging from A to B (both ends inclusive).

1. Production Method for Photostimulable Phosphor

The production method of the present invention comprises the step A for mixing lithium tetraborate, boron oxide and silver oxide and the step B for obtaining a photostimulable phosphor comprising lithium heptaborate as a base material and silver as a luminescent center present in the base material by firing the above-mentioned mixture at 820 to 860° C. It is to be noted that the molar ratio between the lithium tetraborate and the boron oxide in the step A is X:1, provided that X>1, and that the amount of the silver oxide is 0.06 to 1.0 mass % relative to the total mass of the lithium tetraborate and the boron oxide.

Hereinafter, the photostimulable phosphor comprising lithium heptaborate as a base material and silver as a luminescent center present in the base material is also referred to as a "silver-containing lithium heptaborate" or "$Li_3B_7O_{12}$:Ag". The photostimulable phosphor is a substance that emits light by light irradiation.

(1) Step A

In this step, lithium tetraborate ($Li_2B_4O_7$), boron oxide ($B_2O_3$) and silver oxide (AgO) are mixed. As the lithium tetraborate, a commercially available product may be generally used, but it preferably has an average particle size of 10 μm or less. As the boron oxide, a commercially available product may be generally used, but it preferably has an average particle size of 20 μm or less. As the silver oxide, a commercially available product may be generally used, but it preferably has an average particle size of 1 μm or less.

The molar ratio between the lithium tetraborate and the boron oxide in this step is X:1, provided that X>1; the lithium tetraborate is used in an excessive amount. The molar ratio between both components (lithium tetraborate: boron oxide) is preferably (2 to 4):1, more preferably (2.5 to 3.5):1. When the molar ratio between both components falls within the range, a photostimulable phosphor having high luminescence intensity can be obtained.

The amount of the silver oxide is 0.06 to 1.0 mass %, preferably 0.06 to 0.8 mass %, relative to the total mass of the lithium tetraborate and the boron oxide. The silver oxide serves as a luminescent center in the lithium heptaborate as a base material. Hence, when the amount of the silver oxide falls within the range mentioned above, a photostimulable phosphor having high luminescence intensity can be obtained.

The amount of the silver oxide influences the effective atomic number. When the silver oxide is used in amounts of 0.06, 0.08, and 0.10 mass %, the effective atomic numbers are 7.50, 7.72, and 7.90, respectively. Meanwhile, the effective atomic number of muscular tissues of the human body is 7.56. Hence, the amount of the silver oxide is preferably 0.06 to 0.8 mass %, also from the viewpoint of enhancing the biological tissue equivalence by bringing the effective atomic number close to that of the human body. Those components may be mixed using a known means such as a ball mill.

The effective atomic number can be calculated by the method described in, for example, the Japan Society of Medical Physics ed., "*Kyushu Senryou no Hyoujun Sokuteihou*" (Standard Method for Absorbed Dose Measurement), p. 166.

(2) Step B

In this step, the mixture obtained in the step A is fired at 820 to 860° C. By firing it at the temperature, a photostimulable phosphor having high luminescence intensity can be obtained. The firing temperature is preferably 840 to 860° C. The firing time is preferably 4 hours or longer, more preferably 6 hours or longer. It is to be noted that since an excessively long firing time may possibly result in production of a deteriorated fired product, the firing time is preferably 16 hours or less.

As disclosed in Non-patent Document 2, the phase transition temperature of lithium heptaborate and lithium tetraborate+liquid phase is 856±2° C. Hence, when the sintering temperature is 820 to 860° C. in this step, conversion into lithium heptaborate is promoted to give a photostimulable phosphor having high luminescence intensity.

In this step, the starting materials are fired but are not completely melted. As a result, a fired product obtained is less likely to adhere to a vessel used for the firing, and hence, it is possible to fire the starting materials on a thin platinum plate or the like. This leads to good workability. The firing is preferably performed under an inert atmosphere.

Since the starting materials used in the production method of the present invention are commonly available materials, a photostimulable phosphor having superior properties can be provided inexpensively by the present invention.

2. Silver-Containing Lithium Heptaborate ($Li_3B_7O_{12}$:Ag)

The silver-containing lithium heptaborate photostimulable phosphor of the present invention comprises lithium heptaborate as a base material and silver as a luminescent center and emits light by excitation (stimulation) resulting from irradiation with radiation and subsequent additional irradiation with light such as blue light. The silver-containing lithium heptaborate photostimulable phosphor of the present invention is preferably produced by the aforementioned production method.

(1) General Characteristics

The silver-containing lithium heptaborate photostimulable phosphor of the present invention is a colorless microcrystal and soluble in water and insoluble in organic solvents. The photostimulable phosphor is neither deliquescent nor efflorescent, and is a stable substance.

(2) Effective Atomic Number

The effective atomic number of the silver-containing lithium heptaborate of the present invention is 7.68 when the silver content is 0.08 mass %, and the effective atomic number is very close to that of muscular tissues of the human body, 7.56. Hence, the silver-containing lithium heptaborate of the present invention can provide a precise radiation dosimeter element.

(3) Fluorescence Properties

The silver-containing lithium heptaborate of the present invention emits fluorescence by irradiation with radiation and subsequent excitation with light. The fluorescence can be observed by a known means such as an electronic cooled CCD camera. When the silver-containing lithium heptaborate of the present invention is excited with blue light, it exhibits ultraviolet luminescence. The ultraviolet luminescence spectrum is preferably a monomodal spectrum with a maximum value at 300 to 310 nm. FIG. 1 shows luminescence spectra of the silver-containing lithium heptaborate when it is excited with various lights. More specifically, FIG. 1 shows that a monomodal spectrum with a maximum value at 305 nm is observed when the lithium heptaborate is excited with blue diode light of 470 nm wavelength. When the lithium heptaborate is excited with green diode light of 525 nm, it can emit light slightly. However, when the lithium heptaborate is excited with red diode light of 635 nm, it does not emit light.

In consideration of these findings, it is preferred that the silver-containing lithium heptaborate of the present invention is excited with blue light. The wavelength is preferably 420 to 480 nm.

When the silver-containing lithium heptaborate is excited with blue light after irradiation with radiation, red-orange radiophotoluminescence (with maximum values at 620 and 520 nm) is observed, which is not shown in FIG. 1. Since the radiophotoluminescence can be cut off with an ultraviolet transmission short pass filter (e.g., U-340 from HOYA Corporation), it is easy to measure only ultraviolet luminescence.

Figure 2:
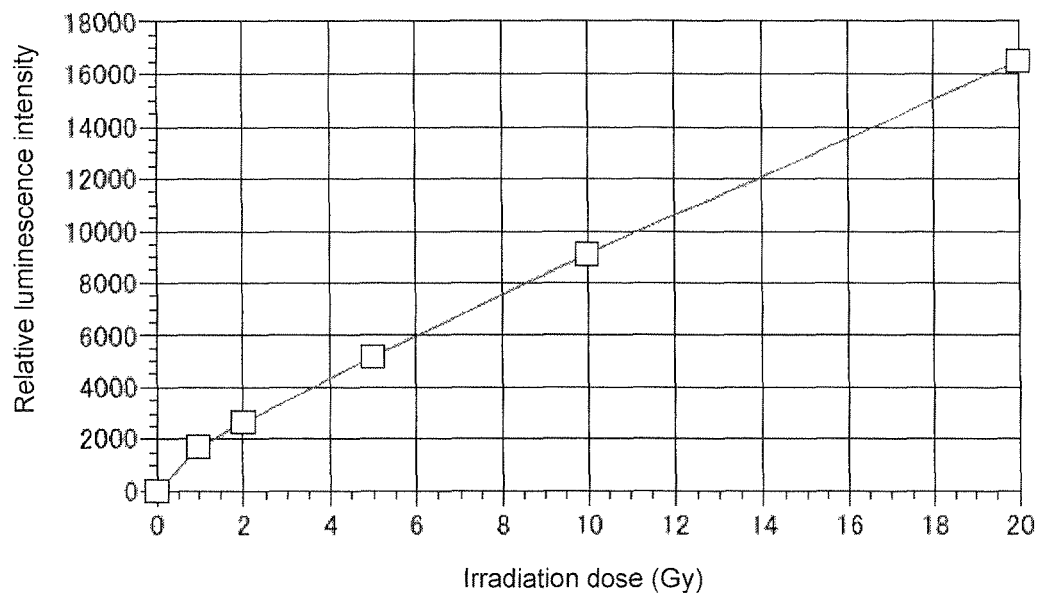
FIG. 2 shows the relation between the dose of irradiated X rays and the amount of luminescence.

FIG. 2 shows the relation between the dose of irradiated X rays and the amount of luminescence. There is a distinct relation between the both, and the present invention can be used as an X-ray dosimeter element by means of preparing a calibration curve.

Figure 3:
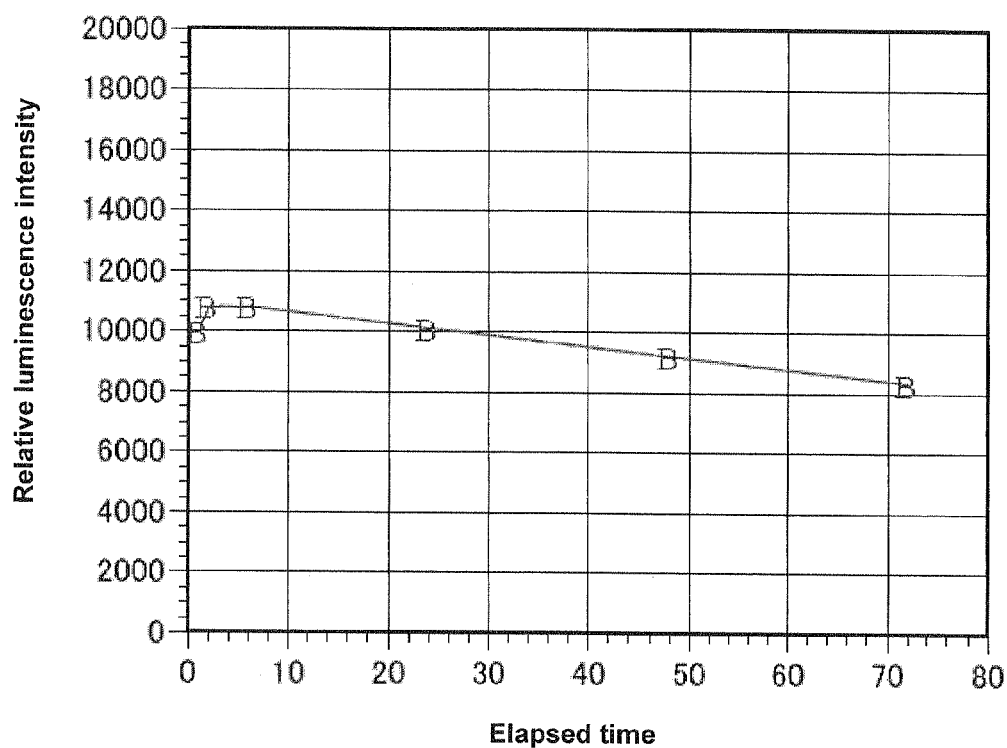
FIG. 3 shows a fading characteristic.

FIG. 3 shows decrease in the amount of photoexcited luminescence (fading characteristic) which is observed when the silver-containing lithium heptaborate of the present invention is irradiated with X rays and then stored in a dark place at room temperature (15° C.). The amount of luminescence somewhat increases (by about 7%) one hour after the start of storage, but thereafter, the amount gradually decreases with the storage time. The degree of the decrease is about 7% for 24 hours, which is not so large. Hence, the silver-containing lithium heptaborate of the present invention is also superior in fading characteristic.

Figure 4:
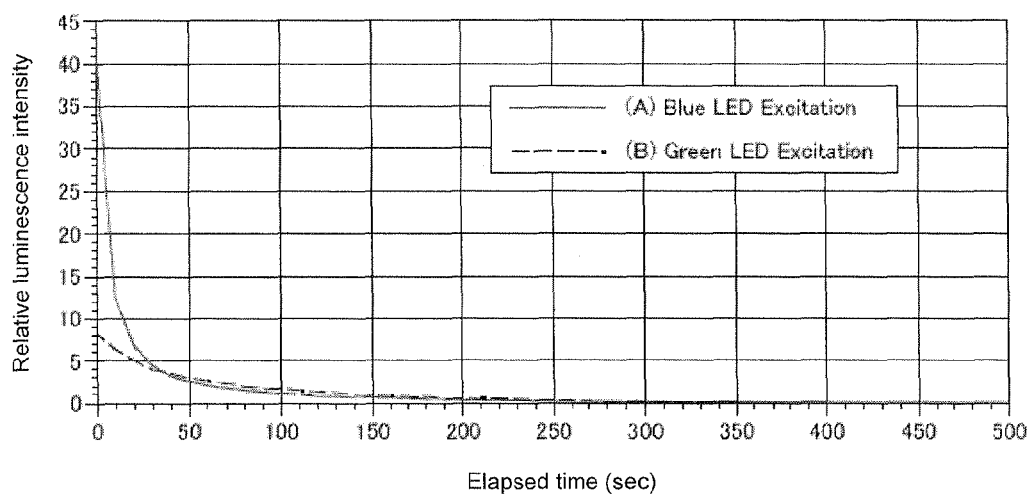
FIG. 4 shows attenuation of ultraviolet luminescence intensity.
Figure 5:
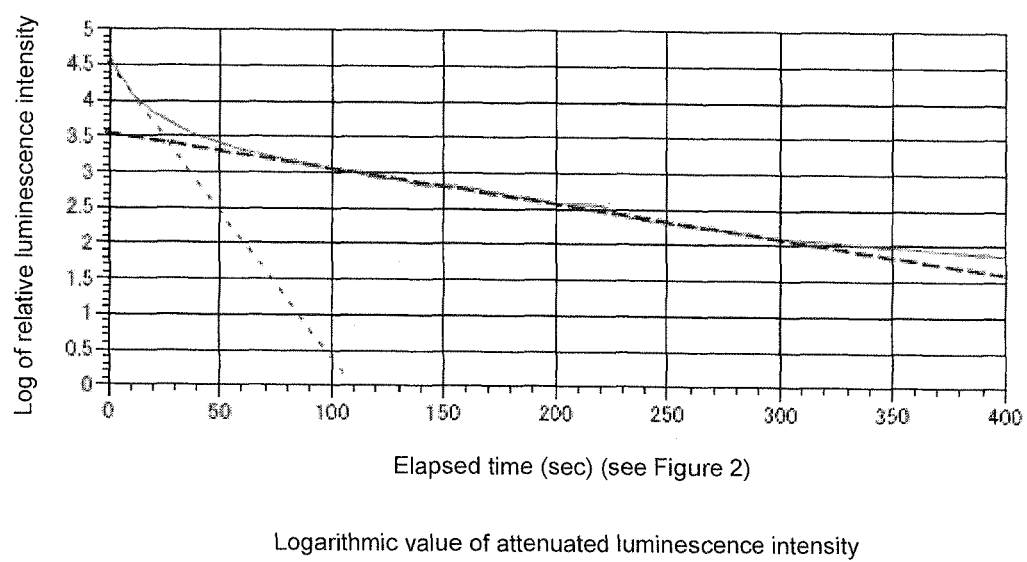
FIG. 5 shows attenuation of ultraviolet luminescence intensity.

The ultraviolet luminescence obtained by excitation with blue light consists of two components having different half-lives. FIGS. 4 and 5 show results obtained by a measurement of attenuation of ultraviolet luminescence intensity using a CCD camera. As shown in FIG. 5, there are a first component (thin dashed line) and a second component (thick dashed line) in the ultraviolet luminescence obtained by excitation with blue light. The initial intensity of the second component is one twentieth of that of the first component and the half-life of the second component is 12 times longer than that of the first component. Thus, it is possible to measure dose more rapidly by measuring the first component having a shorter half-life.

3. Use

The silver-containing lithium heptaborate of the present invention is useful as an element in two-dimensional and three-dimensional dosimeters. In particular, the silver-containing lithium heptaborate of the invention is a stable powder and can be formed into a plate by mixing the lithium heptaborate into a polymer or the like. Hence, a sheet of the photostimulable phosphor, a thin film body consisting of the photostimulable phosphor sheet and a thin material such as paper, and a laminate using the thin film body are useful as materials for dosimetry.

Further, if the light source portion and filter portion in a device already marketed for use of an imaging plate (IP) are slightly modified, the device can use a laminate comprising a photostimulable phosphor obtained by the present invention, instead of an imaging plate (IP).

Hereinafter, the photostimulable phosphor plate, the photostimulable phosphor sheet, the thin film body, and the laminate will be described in detail.

3-1. Photostimulable Phosphor Plate and Photostimulable Phosphor Sheet (1) Photostimulable Phosphor Plate and Photostimulable Phosphor Sheet The term "plate" refers to a tabular material. In the present invention, a tabular material of the photostimulable phosphor with a thickness of more than 1 mm is referred to as a "photostimulable phosphor plate", while a tabular material of the photostimulable phosphor with a thickness of 1 mm or less is referred to as a "photostimulable phosphor sheet".

When the tabular material is too thick, an area that is beyond the reach of excitation light is given at the time of excitation with light in some cases, but when the tabular material is too thin, the problem of intensity decrease can arise. In consideration of these points, it is preferable to use the photostimulable phosphor sheet in the present invention. In particular, the thickness of the sheet is preferably 0.05 to 1 mm, more preferably 0.1 to 0.5 mm. The photostimulable phosphor sheet will be described in detail below, and the description also applies to the photostimulable phosphor plate.

The shape of the photostimulable phosphor sheet may be a circle or a polygon such as a tetragon, but is not particularly limited thereto. From the viewpoint of handleability as a dosimetry material, the photostimulable phosphor sheet in a circular shape preferably has a diameter of 200 to 260 mm and the sheet in a quadrangular shape preferably has a 260 to 400 mm long side and a 180 to 400 mm short side. The lengths of the long side and the short side may be the same.

It is preferred that the photostimulable phosphor sheet comprises the photostimulable phosphor of the present invention and a binder, wherein powder of the photostimulable phosphor is dispersed in the binder. The average particle size of the powder is preferably 2 to 20 μm. The particle size may be measured with a sieve or by microscopic observation.

The binder retains the dispersed photostimulable phosphor powder and functions as a matrix in the photostimulable phosphor sheet. The binder is preferably a high-molecular compound such as a thermoplastic resin or a cured thermosetting resin. Examples of the thermoplastic resin include resins superior in adhesiveness, such as thermoplastic polyethylenes, thermoplastic polyesters, polyvinyl alcohols, polyvinyl acetals, polyvinyl acetates and phenoxy resins. Examples of the thermosetting resin include resins superior in adhesiveness, such as epoxy resins, urethane resins and unsaturated polyester resins. From the viewpoint of handleability, the binder is preferably a cured thermosetting resin, particularly preferably a cured epoxy resin.

The mass ratio between the photostimulable phosphor powder and the binder is preferably 100:(20 to 700), more preferably 100:(30 to 300), yet more preferably 100:(40 to 100), still more preferably 100:(60 to 80). When the mass ratio falls within the range, the density of the photostimulable phosphor sheet is about 1 g/cm$^3$, which is close to the density of the human body. Hence, it is possible to measure dose more precisely.

(2) Production Method for Photostimulable Phosphor Sheet (2-1) The First Production Method for Photostimulable Phosphor Sheet A photostimulable phosphor sheet is preferably produced through the following steps:
a step c for preparing a photostimulable phosphor powder,
a step d for forming a flowable binder layer on a substrate,
a step e for retaining the photostimulable phosphor powder in the flowable binder layer by placing the powder on the surface of the flowable binder layer,
a step f for solidifying the flowable binder layer, and
a step g for removing the substrate (hereinafter referred to as "the first production method for photostimulable phosphor sheet").

The photostimulable phosphor powder may be prepared by pulverizing the photostimulable phosphor using a known means (pulverizer, mortar, etc.) The particle size of the powder is as described above.

The substrate is a plate-like or sheet-like material. Examples of the material to be used include, but are not particularly limited to, release paper whose surface is covered with a silicone resin or the like, fluorine-based resin sheets, glass plates whose surface is covered with a mold release agent, and the like.

The flowable binder is the binder precursor which is solidified into the binder, and the binder is so flowable that it can embed the placed photostimulable phosphor powder. More specifically, the flowable binder is preferably a thermosetting resin or a varnish formed by dissolution of a thermoplastic resin in an organic solvent. The term "thermosetting resin" as used herein refers to an uncured resin. The thermosetting resin, which may contain a known curing agent or curing accelerator, is preferably a resin that can be cured at 50 to 100° C. to prevent deterioration of the photostimulable phosphor. In particular, an epoxy resin, urethane resin or acrylic resin, which is superior in curing property, mechanical strength and adhesiveness, is preferably used.

Examples of the epoxy resin include bisphenol A epoxy resins, bisphenol F epoxy resins, and hydrogenated resins thereof. Since hydrogenated resins are less likely to absorb ultraviolet rays, they have the advantage that luminescence can be detected with good sensitivity when the photostimulable phosphor sheet is used as a dosimeter element. As the urethane resin or the acrylic resin, a known resin may be used, but is less likely to absorb ultraviolet rays. Hence, an aliphatic urethane resin or aliphatic acrylic resin that contains no aromatic ring is preferred.

Examples of the varnish formed by dissolution of a thermoplastic resin in an organic solvent include varnishes obtained by dissolution of a thermoplastic resin that absorbs less ultraviolet rays in an alcohol such as ethanol or a ketone solvent such as acetone. Examples of the thermoplastic resin that absorbs less ultraviolet rays include polyvinyl acetals (e.g., polyvinyl butyral) and polyvinyl alcohols.

In light of handleability, it is preferable to use a thermosetting resin as a flowable binder.

The flowable binder layer is a layer consisting of a flowable binder and the thickness of the flowable binder layer is adjusted as appropriate according to the thickness of the photostimulable phosphor sheet to be obtained. The flowable binder layer may be formed by coating or spreading the flowable binder on the substrate. The coating may be performed using a known means such as a bar coater or a spin coater. The spreading may be performed by pouring the flowable binder onto the substrate and casting the binder.

Subsequently, the photostimulable phosphor powder is placed on the surface of the flowable binder layer. The placement is to put the photostimulable phosphor powder on the surface of the flowable binder layer. For example, the powder may be placed by spraying it from above the flowable binder layer. In this case, it is preferable to use a sieve to spray the powder. The size of the sieve is selected as appropriate. Since the flowable binder layer is flowable, part or all of the placed photostimulable phosphor powder penetrates into the flowable binder layer and is embedded and retained in the layer. After this step, a step for removing unretained photostimulable phosphor powder may be added. More specifically, the unretained photostimulable phosphor powder may be dropped and removed by a means such as shaking the substrate while keeping the photostimulable phosphor-sprayed flowable binder layer facing down. The amount of the photostimulable phosphor powder is adjusted to keep the mass ratio between the photostimulable phosphor powder and the binder within the range mentioned above in a finally formed photostimulable phosphor sheet.

Subsequently, the flowable binder layer is solidified. As for a method of the solidification, when a thermosetting resin is used as a flowable binder, the flowable binder layer may be solidified by curing of the thermosetting resin either at room temperature or through heating. The heating temperature is preferably 50 to 100° C. The heating time may be adjusted as appropriate, but is preferably 1 to 24 hours. When the varnish mentioned above is used as a flowable binder, the flowable binder layer may be solidified by removal of the organic solvent contained in the varnish by heating, depressurization, or the like. In this case, the heating temperature is preferably 50 to 100° C. and the heating time is preferably 1 to 24 hours.

In this case, it is preferred that, in the stage about half of the flowable binder layer has been solidified, a pressure is applied on the surface of the layer to enhance the adhesiveness between the photostimulable phosphor powder and the binder, followed by complete solidification of the layer. The stage about half has been solidified is so-called B stage when a thermosetting resin is used. B stage is an intermediate stage in curing of a thermosetting resin and a stage where materials have become unable to be melted or dissolved completely. The stage about half has been solidified when a varnish is used is a stage the organic solvent contained in the varnish has been removed and materials have become unable to flow completely.

By removing the substrate mentioned above, a photostimulable phosphor plate may be prepared. The substrate may be removed by any method. For example, the substrate may be removed by a means such as detaching the substrate or dissolving the substrate in an organic solvent or the like.

(2-2) The Second Production Method for Photostimulable Phosphor Sheet

Alternatively, a photostimulable phosphor sheet is preferably produced through the following steps:
a step h for preparing a mixture of a photostimulable phosphor powder and a flowable binder by mixing them,
a step i for forming a layer of the mixture on a substrate,
a step j for solidifying the mixture layer, and
a step k for removing the substrate (hereinafter referred to as "the second production method for photostimulable phosphor sheet").

The step h for mixing a photostimulable phosphor powder and a flowable binder may be performed using, for example, a known kneader such as a mixer or a roll. The mixing ratio is as described above. The step i for forming a layer of the mixture on a substrate may be performed by coating or casting the mixture on a substrate, in the same manner as in the step d of the first production method for photostimulable phosphor sheet. When the mixture consists of a varnish comprising a thermoplastic resin and an organic solvent and the photostimulable phosphor powder, the step i may also be performed by spray coating the mixture on a substrate.

Likewise, the step j for solidifying the mixture layer and the step k for removing the substrate may be performed in the same manner as in the steps f and g, respectively, in the first production method for photostimulable phosphor sheet.

(2-3) The Third Production Method for Photostimulable Phosphor Sheet

Alternatively, a photostimulable phosphor sheet is preferably produced through the following steps:
a step l for preparing a mixture of a photostimulable phosphor powder and a binder consisting of a thermoplastic resin by mixing them during heating,
a step m for placing the mixture on a substrate, a step n for forming a layer on the substrate and sticking the layer to the substrate tightly, by heating the mixture, and
a step o for removing the substrate (hereinafter referred to as "the third production method for photostimulable phosphor sheet").

The step l for mixing a photostimulable phosphor powder and a binder consisting of a thermoplastic resin during heating may be performed using, for example, a known kneader such as a mixer or roll that has a heating means. As the thermoplastic resin, the resin described above may be used, but a polyvinyl acetal resin or a polyvinyl acetate resin is more preferred since they are superior in adhesiveness. The mixing temperature may be a temperature at which a thermoplastic resin to be used is melted, but the temperature is preferably 120 to 180° C. when a polyvinyl acetal resin or a polyvinyl acetate resin is used.

In the step m, the mixture is made into a powder or a mass by pulverization or the like and the powder or the mass is placed on a substrate. Subsequently, in the step n, the powder or the mass is melted by heating to form a layer and stick the layer to the substrate tightly. In this case, the heating temperature may be a temperature at which the binder is melted whereby the layer and the substrate are stuck tightly, but the temperature is preferably 120 to 180° C. when a polyvinyl acetal resin or a polyvinyl acetate resin is used.

If the mixture obtained in the step l is coated or casted on the substrate while the mixture is flowable, the steps m and n can be performed simultaneously. Specific methods for coating and casting, the thickness of the layer, and the like are as described above.

The step o for removing the substrate may be performed in the same manner as in the step g of the first production method for photostimulable phosphor sheet. It is preferable to add a step for cooling the mixture layer to solidify the layer, prior to the step o.

(2-4) The Fourth Production Method for Photostimulable Phosphor Sheet

Alternatively, a photostimulable phosphor sheet is preferably produced through the following steps:
the step c for preparing a photostimulable phosphor powder,
a step d1 for forming a binder layer on a substrate,
a step e1 for retaining the photostimulable phosphor powder in the binder layer by placing the powder on the surface of the binder layer and then applying a pressure on the powder, and
the step g for removing the substrate (hereinafter referred to as "the fourth production method for photostimulable phosphor sheet").

The step d1 for forming a binder layer on a substrate may be performed by, for example, forming a flowable binder layer on a substrate, as described in the foregoing step d, and then solidifying the flowable binder layer into a non-flowable binder layer, as described in the step f.

In the step e1, a pressure is applied to the photostimulable phosphor powder on the binder layer to retain the powder in the layer. The pressurization allows the photostimulable phosphor powder to penetrate the binder layer while cleaving it and to be embedded. The pressurization may be performed by manpower, with a pressing machine or the like. When the binder layer is too hard, the photostimulable phosphor powder may possibly be broken; hence, the binder layer is preferably, for example, acrylic gel or the like in this method. The other steps in this method are as already described.

3-2. Thin Film Body of Photostimulable Phosphor (1) Thin Film Body of Photostimulable Phosphor The thin film body of the photostimulable phosphor is a thin plate-like material comprising a photostimulable phosphor sheet and 0.1 to 5 mm-thick paper or biological tissue-equivalent plastic sheet that is laminated on the photostimulable phosphor sheet. The lamination is to form a layer consisting of a certain material on a layer consisting of another material and includes cases where layers are bonded or not bonded to each other. In particular, when both cases are differentiated, the former is sometimes referred to as "to laminate adhesively" and the latter as "to laminate non-adhesively".

Figure 10:
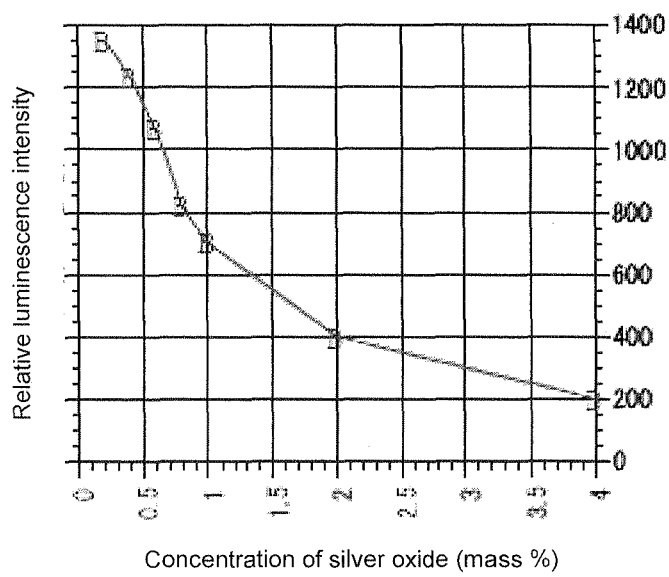
FIG. 10 shows the influence of the concentration of silver oxide.
Figure 11:
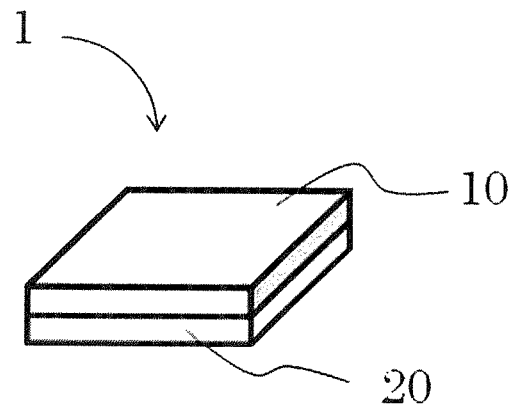
FIG. 11 shows a thin film body schematically.

FIG. 11 illustrates a thin film body. In FIGS. 11, 1, 10 and 20 refer to a thin film body, a photostimulable phosphor sheet, and paper, respectively. The paper 20 may be substituted by a biological tissue-equivalent plastic sheet. The paper as referred to herein is paper consisting essentially of cellulose. The biological tissue-equivalent plastic sheet as referred to herein is an acrylic resin plate obtained by polymerization of (meth)acrylic acid and a derivative thereof or a sheet of a high-molecular compound that is commercially available as a tissue-equivalent phantom. When a luminescence image is observed after irradiation with excitation light from the biological tissue-equivalent plastic sheet in the thin film body, it is necessary to use a light-transmissive, biological tissue-equivalent plastic sheet.

The thin film body has the advantage that it needs less labor when it is carried, owing to its lightness. Further, the thin film body may be used alone as a two-dimensional dosimeter element or used as a three-dimensional dosimeter element by combining the thin film body with other materials, as described later.

The thin film body also has the advantage that it can be cut easily with a cutter or the like. From the viewpoint of enhancing its cutting processability, it is preferred that the paper 20 or the biological tissue-equivalent plastic sheet and the photostimulable phosphor sheet 10 are laminated adhesively.

(2) Production Method for Thin Film Body (2-1) The First Production Method for Thin Film Body A thin film body is preferably produced by a method comprising the following steps:

a step C for preparing a photostimulable phosphor powder, a step D for forming a flowable binder layer on paper or a biological tissue-equivalent plastic sheet, a step E for retaining the powder obtained in the step C in the flowable binder layer obtained in the step D by placing the powder on the surface of the flowable binder layer, and a step F for solidifying the flowable binder layer (hereinafter referred to as "the first production method for thin film body").

The step D may be performed as described in the step d of the first production method for photostimulable phosphor sheet. It is to be noted that paper or a biological tissue-equivalent plastic sheet is used as a substrate and that the thickness of the flowable binder layer is adjusted to 0.05 to 1 mm eventually. In particular, when a biological tissue-equivalent plastic sheet is used, the use of a material such as a flowable binder compatible with the sheet (e.g., a monomer used for a starting material of the sheet) improves the affinity.

The step C may be performed by preparing a photostimulable phosphor obtained in "1. Production method for photostimulable phosphor" or a photostimulable phosphor as described in "2. Silver-containing lithium heptraborate" and pulverizing the photostimulable phosphor by a known means.

The steps E and F may be performed as described for the steps e and f, respectively, in the first production method for photostimulable phosphor sheet.

(2-2) The Second Production Method for Thin Film Body

Alternatively, a thin film body is preferably produced by a method comprising the following steps:

a step H for preparing a mixture of a photostimulable phosphor powder and a flowable binder by mixing them, a step I for forming a layer of the mixture on paper or a biological tissue-equivalent plastic plate, and a step J for solidifying the mixture layer (hereinafter referred to as "the second production method for thin film body").

The step H may be performed in the same manner as in the step h of the first production method for photostimulable phosphor sheet. The step I for forming a layer of the mixture on a substrate may be performed in the same manner as in the step d of the first production method for thin film body. The step J for solidifying the mixture layer may be performed in the same manner as in the step F of the first production method for thin film body.

(2-3) The Third Production Method for Thin Film Body

Alternatively, a thin film body is preferably produced by a method comprising the following steps:

a step L for preparing a mixture of a photostimulable phosphor powder and a binder consisting of a thermoplastic resin by mixing them, a step M for placing the mixture on paper or a biological tissue-equivalent plastic plate, and a step N for forming a layer on the substrate and sticking the layer to the substrate tightly, by heating the mixture (hereinafter referred to as "the third production method for thin film body").

The steps L to N may be performed in the same manner as in the steps l to n, respectively, in the third production method for photostimulable phosphor sheet.

(2-4) The Fourth Production Method for Thin Film Body

Alternatively, a thin film body is preferably produced by a method comprising the following steps:

the step C for preparing a photostimulable phosphor powder, a step D1 for forming a binder layer on paper or a biological tissue-equivalent plastic sheet, and a step E1 for retaining the powder obtained in the step C in the binder layer by placing the powder on the surface of the binder layer and then applying a pressure to the powder (hereinafter referred to as "the fourth production method for thin film body").

The steps D1 and E1 may be performed in the same manner as in the steps d1 and e1, respectively, in the fourth production method for photostimulable phosphor sheet.

(2-5) The Fifth Production Method for Thin Film Body

Yet alternatively, a thin film body is preferably produced by a method comprising the following steps:

a step P for preparing a photostimulable phosphor sheet as described above, and a step Q for bonding paper or a biological tissue-equivalent plastic sheet onto the photostimulable phosphor sheet (hereinafter referred to as "the fifth production method for thin film body").

In the step P, the photostimulable phosphor sheet may be prepared as described in the first to fourth production methods for photostimulable phosphor sheet, which are described above.

The step Q may be performed by using a known adhesive to stick paper or a biological tissue-equivalent plastic sheet on the photostimulable phosphor sheet. The adhesive is preferably one having affinity with the binder contained in the photostimulable phosphor sheet and with the paper or biological tissue-equivalent plastic sheet, but the adhesive is not limited thereto. A preferred adhesive is an epoxy resin.

3-3. Laminate (1) Laminate of Photostimulable Phosphor

The laminate of the photostimulable phosphor is a laminate comprising the foregoing thin film body and a biological tissue-equivalent plastic plate. From the viewpoint of handleability, the biological tissue-equivalent plastic plate is preferably one having a thickness of more than 2 mm (hereinafter also referred to as a "biological tissue-equivalent thick plastic plate"). The thickness of the thick plate is preferably 20 mm or less, more preferably 5 mm or less.

Figure 12:
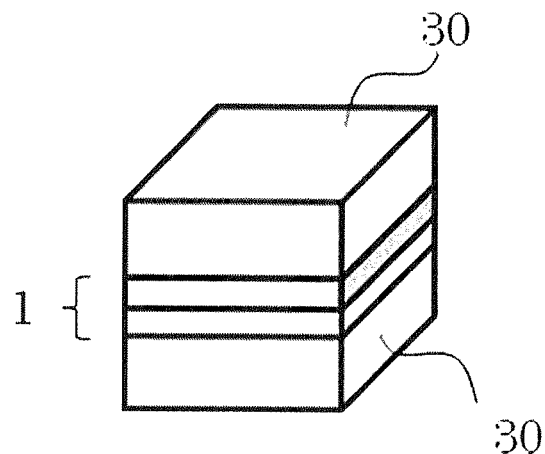
FIG. 12 shows a laminate schematically.

FIG. 12 illustrates a laminate. In FIG. 12, 1 refers to a thin film body and 30 refers to a biological tissue-equivalent thick plastic plate. The laminate has the advantage that it is easy to handle owing to its high strength. Further, the laminate is thick and hence is useful as a three-dimensional dosimeter element. In this case, it is preferred that the laminate has 5 to 25 layers of the thin film body 1 and 5 to 25 layers of the biological tissue-equivalent thick plastic plate 30 and has an overall thickness of 100 to 500 mm. The three-dimensional dose distribution is determined by separating the laminate exposed to radiation into the respective layers, measuring luminescence for each layer which is caused by photoexcitation, and integrating the data of each layer. Hence, it is preferred that the thin film body 1 and the biological tissue-equivalent thick plastic plate 30 can be separated easily. That is, it is preferred that the respective layers are laminated non-adhesively.

Figure 13:
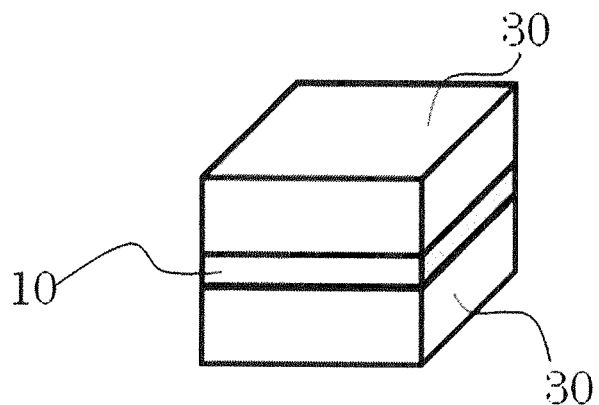
FIG. 13 shows a laminate schematically.

As illustrated by FIG. 13, the thin film body 1 in the laminate illustrated by FIG. 12 may be substituted by the photostimulable phosphor sheet 10.

(2) Production Method for Laminate

The laminate may be produced by lamination of the biological tissue-equivalent thick plastic plate 30 and the laminate 1 or photostimulable phosphor sheet 10 which is prepared as described above. The lamination may be performed by stacking both components. As described above, the laminate is exposed to radiation and then separated into the respective parts. Hence, the respective layers are preferably laminated non-adhesively. When the respective layers are needed to be fixed temporarily, it is preferable to use an adhesive tape or the like to fix the layers.

EXAMPLES

Example 1

Lithium tetraborate (Nacalai Tesque, Inc.) and boron oxide (Koso Kagaku Yakuhin K. K.) were mixed in a molar ratio of 3:1 and 0.1 mass % of silver oxide (Sigma-Aldrich Japan K. K.) was added to the mixture, followed by mixing.

The mixture obtained was placed on a platinum plate and fired in an electric furnace at 860° C. for 6 hours.

Figure 6:
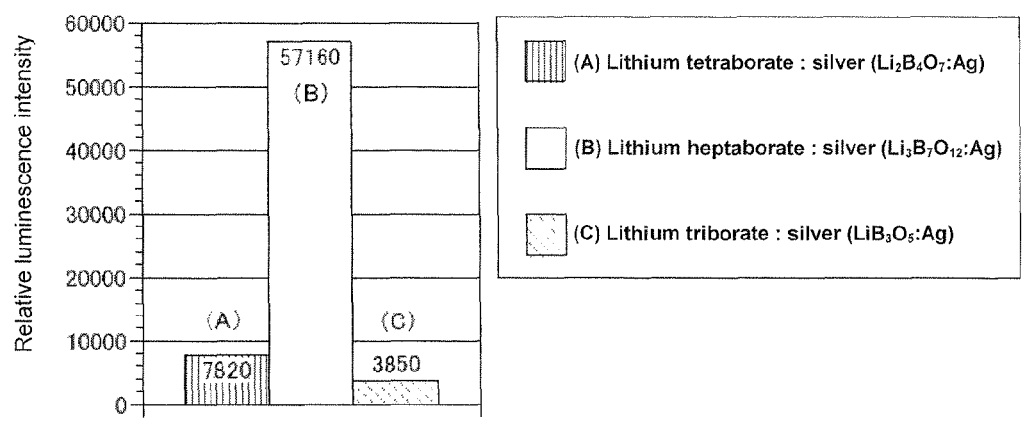
FIG. 6 shows the luminescence intensity of a silver-containing lithium heptaborate obtained in an Example.

The thus obtained silver-containing lithium heptraborate was irradiated with 20 Gy of X rays (CuKα rays) and then irradiated and excited with blue LED light of 470 nm, and the luminescence intensity was measured. The luminescence intensity was measured with an electronic cooled CCD camera (Finger Lakes Instrumentation) having an ultraviolet transmission filter (HOYA Corporation). The result is shown in FIG. 6. The result of this example is represented by the symbol (B) in FIG. 6.

Comparative Example 1

Substances were obtained in the same manner as in Example 1 except that the molar ratio between the lithium tetraborate and the boron oxide was changed to 1:0 and 1:1. The products were a silver-containing lithium tetraborate and a silver-containing lithium triborate. The results are shown in FIG. 6. The results of this example are represented by the symbols (A) and (C), respectively, in FIG. 6.

FIG. 6 reveals that the silver-containing lithium heptraborate obtained in Example 1 has high luminescence intensity.

Example 2-1

Figure 7:
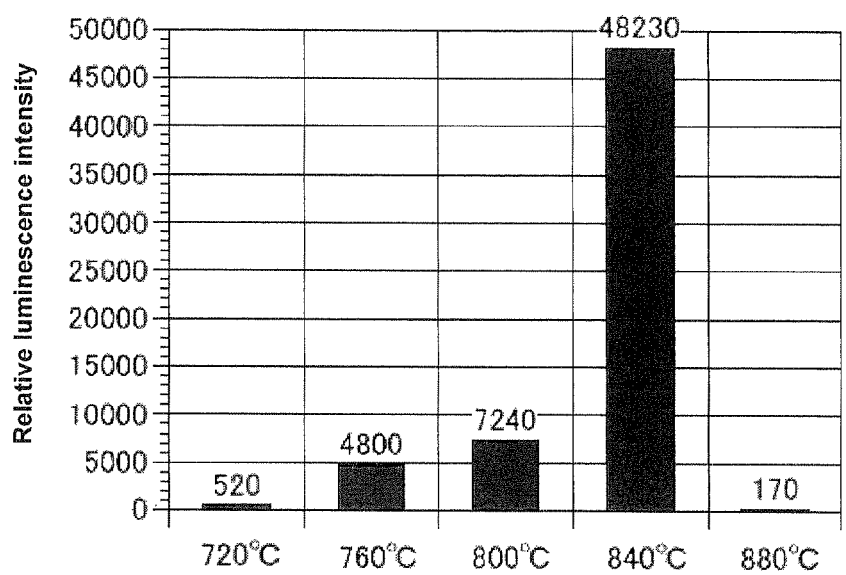
FIG. 7 shows the luminescence intensity of silver-containing lithium heptaborates obtained in Examples.

A silver-containing lithium heptraborate was obtained and evaluated, in the same manner as in Example 1 except that the firing conditions were 840° C. and 6 hours. The result is shown in FIG. 7. High relative luminescence intensity, 48230, was obtained.

Example 2-2

A silver-containing lithium heptraborate was obtained and evaluated, in the same manner as in Example 1 except that the firing conditions were 860° C. and 6 hours. The result is shown in FIG. 7 (the note on the bottom of the figure). High relative luminescence intensity, 51820, was obtained.

Comparative Example 2-1

A substance was obtained and evaluated, in the same manner as in Example 2-1 except that the firing temperature was 720° C.

Comparative Example 2-2

A substance was obtained and evaluated, in the same manner as in Example 2-1 except that the firing temperature was 760° C.

Comparative Example 2-3

A substance was obtained and evaluated, in the same manner as in Example 2-1 except that the firing temperature was 800° C.

Comparative Example 2-4

A substance was obtained and evaluated, in the same manner as in Example 2-1 except that the firing temperature was 880° C.

The results of these comparative examples are shown in FIG. 7.

FIG. 7 reveals that the silver-containing lithium heptaborates obtained in Example 2 in which the firing temperature was 840 to 860° C. have extremely high luminescence intensity.

Reference Example 1

Figure 8:
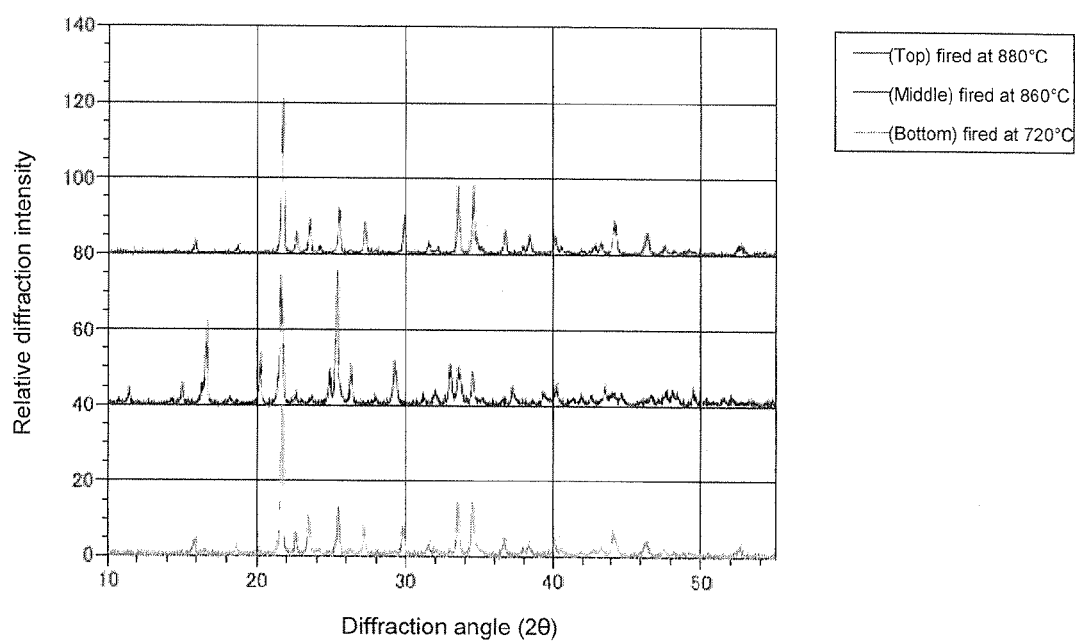
FIG. 8 shows X-ray diffraction spectra.

FIG. 8 shows X-ray diffraction spectra of the products obtained in Comparative Example 2-1 (a product fired at 720° C.), Example 2-2 (a product fired at 860° C.) and Comparative Example 2-4 (a product fired at 880° C.). The diffraction patterns of the product fired at 720° C. and the product fired at 880° C. are the same and match the diffraction pattern of lithium tetraborate (JCPDS-ICDD Card No. 18-717, CPDS-ICDD Card No. 18-717). The diffraction pattern of the product fired at 860° C. matches the diffraction pattern of lithium heptaborate (JCPDS-ICDD Card No. 32-549, JCPDS-ICDD Card No. 77-077), and no diffraction line of silver oxide is observed. These results reveal that one that functions as a photostimulable fluorescent substance is lithium heptaborate crystal in which a trace of silver or silver ions are present as a luminescent center.

Example 3

Figure 9:
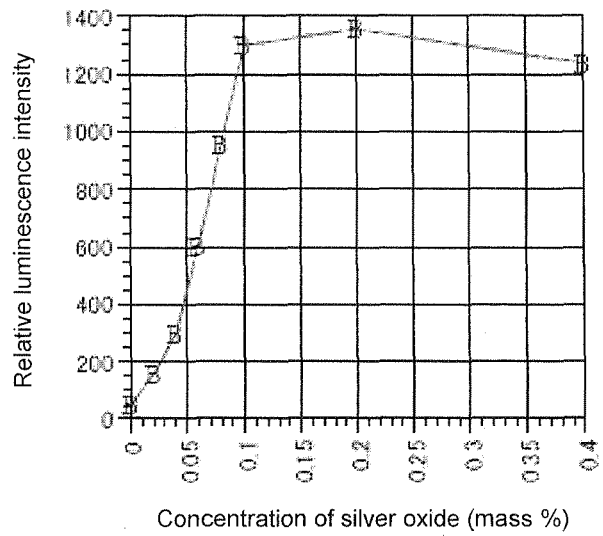
FIG. 9 shows the influence of the concentration of silver oxide.

Silver-containing lithium heptraborates were obtained and evaluated, in the same manner as in Example 1 except that the concentrations of the silver oxide were 0.06, 0.08, 0.1, 0.2, 0.4, 0.6, 0.8 and 1.0 mass %, respectively. The results are shown in FIGS. 9 and 10. FIG. 9 shows the results at lower concentrations and FIG. 10 shows the results at higher concentrations.

Comparative Example 3

Products were obtained and evaluated, in the same manner as in Example 1 except that the concentrations of the silver oxide were 0.0, 0.02, 0.04, 2.0 and 4.0 mass %, respectively. The results are shown in FIGS. 9 and 10.

FIGS. 9 and 10 show that the luminescence intensity is at a maximum level when the concentration of the silver oxide is 0.2 mass %, while the luminescence intensity is at a level of approximately 50% or more of the maximum level when the concentration of the silver oxide falls within a range of 0.06 to 1.00 mass %. Considering that the calculated effective atomic numbers are 7.50, 7.72 and 7.90 in silver oxide concentrations of 0.06, 0.08 and 0.10 mass %, respectively, as described above, it is deemed to be more preferable that the concentration of silver oxide falls within a range of 0.06 to 0.08 mass %.

Example 4

Preparation of Thin Film Body

On thin paper, 270×260 mm (Miyoshinogami from Ohtsuka Brush Mfg. Co., Ltd.; thickness: 0.02 mm; mass: 0.80 g), 3.8 g of a two-pack thermosetting epoxy resin (9005 from Blenny Giken Ltd.) was coated uniformly at a thickness of 0.2 mm to form a flowable binder layer. On the flowable binder layer, 20 g of the silver-containing lithium heptaborate powder obtained in Example 1 was sprayed using a sieve (50 mesh: 300 μm opening). Subsequently, after the flowable binder layer was heated at 80° C. for 5 minutes to stabilize it, the entire paper was minutely shaken to allow the powder to be mixed well into the flowable binder layer, and then the paper was tilted to remove excess powder. As a result, 9.6 g of the powder was retained in the flowable binder layer.

Next, the layer was heated at 70° C. for 1 hour to cure the epoxy resin partially (to B-stage the resin), a pressure was applied on the surface to retain the powder in the layer more stably, and the layer was heated again at 70° C. for 6 hours, thereby curing it completely. A thin film body (thickness: 0.2 mm; density: 1.0 g/cm$^3$) was thus obtained. The photostimulable phosphor powder on the surface took on a very pale pink color.

The thin film body was stable in air and no hygroscopic property was observed. The thin film body, the texture of which was evaluated by hand, was not too hard to be torn and could be easily cut with scissors or a knife and processed. When the thin film body was placed under direct sunlight, it was found to color in several minutes.

The experimental formula for the thin film body obtained in this example is $Li_{0.261}B_{1.82}C_{2.10}H_{2.30}O_{3.18}Ag_{0.0006}$ and the effective atomic number is calculated to be 7.50 (the Japan Society of Medical Physics ed., "*Kyushu Senryou no Hyoujun Sokuteihou*" (Standard Method for Absorbed Dose Measurement), p. 166). The effective atomic number of muscular tissues is 7.42, to which the value of the thin film body obtained in this example is close; hence, the thin film body was biological tissue equivalent. It is deemed that even when a biological tissue-equivalent plastic sheet is used, the overall density of the thin film body of the photostimulable phosphor does not deviate greatly from 1.0/cm$^3$ since the thin film body has an effective thickness of about 0.2 mm.

Example 5

Laminate

The thin film body obtained in Example 4 was cut into a size of 180×240 mm, and tough water plates (tough water phantom WE-3040 from Kyoto Kagaku Co., Ltd.) which are biological tissue-equivalent plastic plates were disposed to sandwich the thin film body: one was 20 mm thick and disposed on the top of the thin film body and the other was 100 mm thick and disposed on the bottom of the thin film body. A laminate was thus prepared.

A linear accelerator machine (Elekta Synergy from Elekta K. K.) was used to irradiate X rays (6 MV) which corresponded respectively to 0.1, 0.5, 1.0, 2.0, and 5.0 Gy, while shifting the irradiation site. The irradiation field was 50×50 mm. After the irradiation, the laminate was disjointed and the thin film body was taken out.

Figure 14:
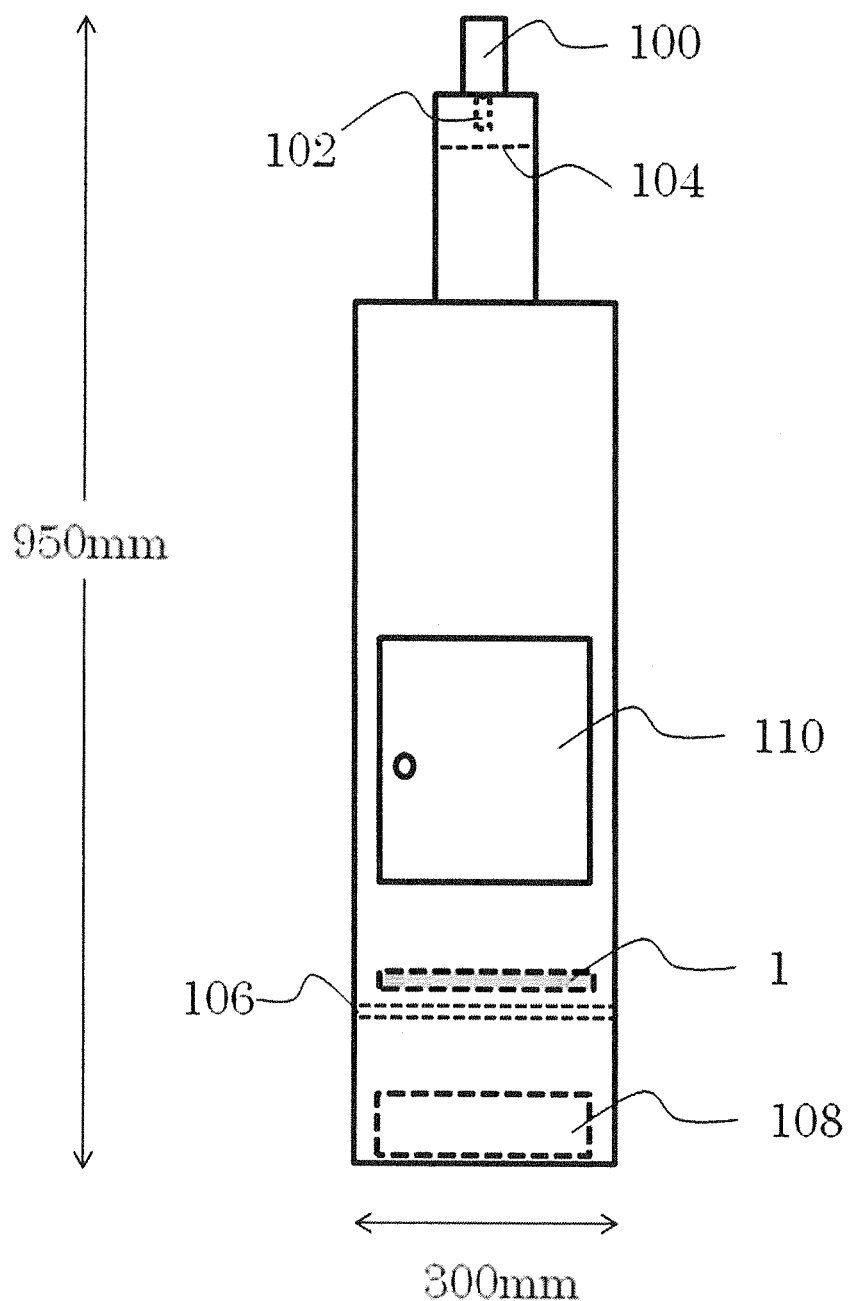
FIG. 14 is a schematic view of a photoexcited fluorescence imaging device.

A photoexcited fluorescence imaging device as illustrated by FIG. 14 was prepared. In FIG. 14, 1 refers to a thin film body, 100 refers to a cooled CCD camera (Microline type from Finger Lake Instruments), 102 refers to an ultraviolet camera lens, 104 refers to a visible light-cutoff ultraviolet transmission filter (U372-80 from Tanaka Kokagaku Kogyo K. K.), 106 refers to an ultraviolet- and heat ray-cutoff plate (a UV-cutoff type acrylic plate from Sakura Plastics Corporation and an ISK171 type heat ray-cutoff glass from Isuzu Glass Co., Ltd.), 108 refers to a blue LED lamp array (an array of 108 1 W LED lamps (B42180 type blue LED from SEUL SEMICONDUCTOR)), and 110 refers to a door.

Figure 15:
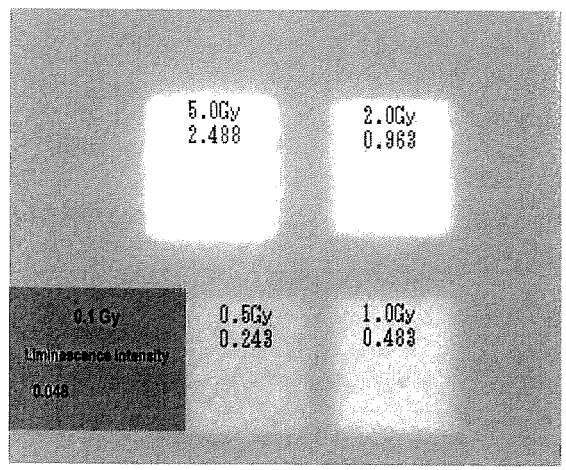
FIG. 15 shows ultraviolet fluorescence images of a thin film body.
Figure 16:
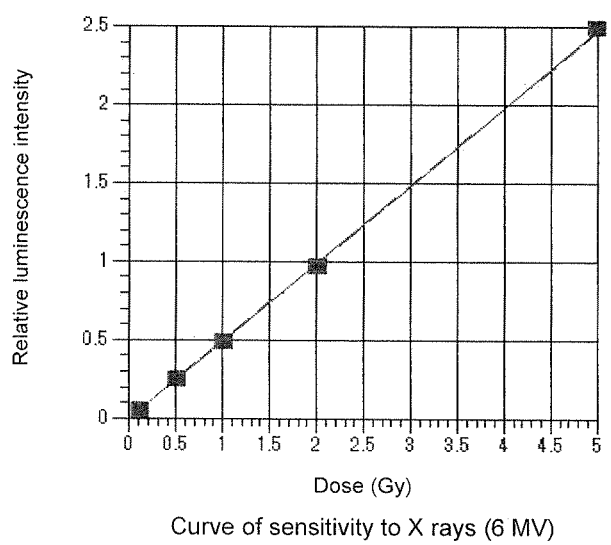
FIG. 16 shows a calibration curve versus X-ray dose.

The device was used to irradiate the thin film body 1 with blue LED light with a total consumption power of 108 W (center: 470 nm) for 30 seconds and ultraviolet rays generated (center: 305 nm) were imaged and recorded with the cooled CCD camera 100. An in-plane position sensitivity coefficient was preliminarily obtained from an image produced by irradiating the whole area such that the dose reached 1 Gy, and the coefficient was used to obtain dose images corrected in intensity. The results are shown in FIGS. 15 and 16. The amount of luminescence shows an almost linear relation to 6 MV X rays and it was confirmed that the thin film body of the photostimulable phosphor functions as a dosimeter.

Example 6

Laminate

Figure 17:
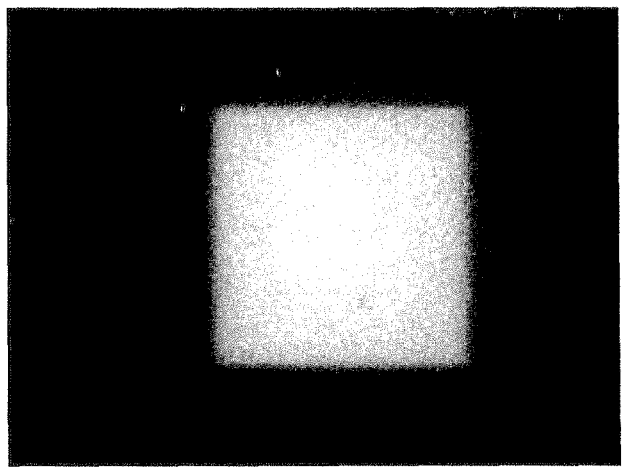
FIG. 17 shows an image of fluorescence photoexcited (stimulated) after irradiation with X rays.
Figure 18:
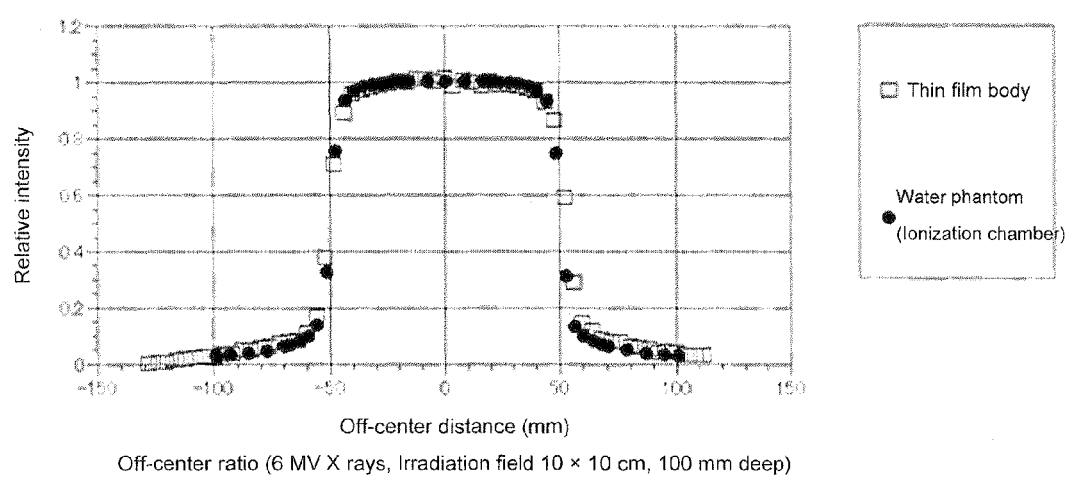
FIG. 18 shows an off-center ratio (versus X rays).

The thin film body obtained in Example 4 was cut into a size of 180×240 mm, and the aforementioned tough water plates were disposed to sandwich the thin film body: one was 20 mm thick and disposed on the top of the thin film body and the other was 200 mm thick and disposed on the bottom of the thin film body. A laminate was thus prepared. The device used in Example 5 was used to irradiate the laminate with X rays (6 MV; 2 Gy for the portion of the thin film body) from above (irradiation field: 100×100 mm). The fluorescence image and intensity distribution of the thin film body were measured. The results are shown in FIGS. 17 and 18. FIG. 18 shows an off-center ratio (OCR). In FIG. 18, the vertical axis represents the average intensity in the area extending to 5 cm both above and below the center of the irradiation field shown in FIG. 17. FIG. 18 also shows an off-center ratio (OCR) of a water phantom. The data was obtained using an irradiation device (a Synergy linear accelerator from Elekta K. K.) which was equivalent to the device used in this Example, an ionization chamber (PTW31010 Semiflex from PRO Radiation Products Design, Inc.) as a well-known dosimeter, and a water phantom (MP3 type from PTW). These results confirmed that the off-center ratio (OCR) of the thin film body nearly matches the OCR of a standard water phantom.

Example 7

Laminate

Figure 19:
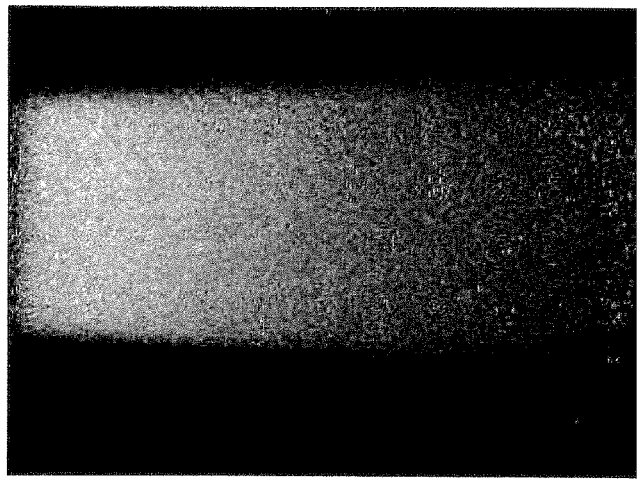
FIG. 19 shows a photoexcited (stimulated) fluorescence image of a thin film body irradiated with X rays.
Figure 20:
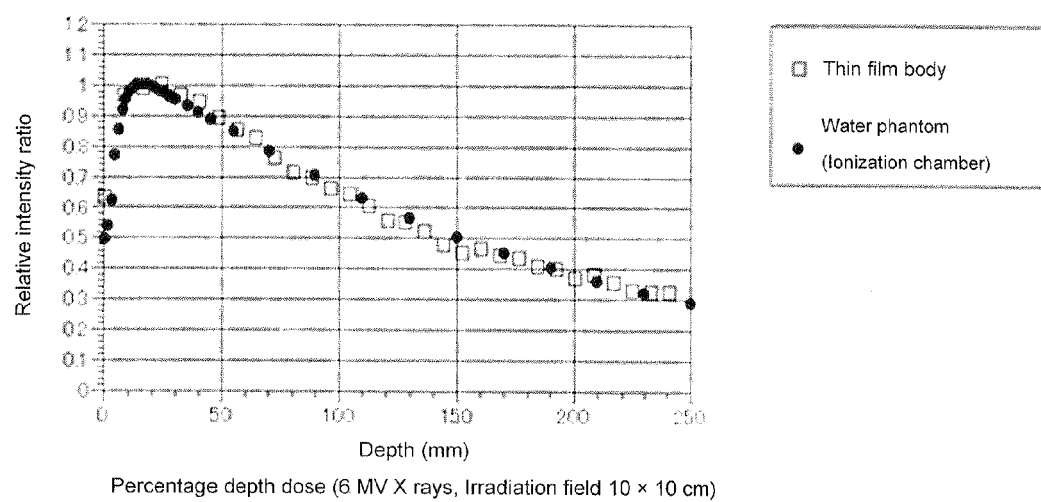
FIG. 20 shows percentage depth dose of a thin film body and a water phantom.

The thin film body obtained in Example 4 was sandwiched between two 100 mm-thick tough water plates and the resulting laminate was disposed such that the layer surface is vertical. The device used in Example 5 was used to irradiate the thus disposed laminate with X rays (6 MV) from above in the vertical direction (2 Gy at a point of 20 mm from the top; irradiation field: 100×100 mm). The thin film body was taken out of the laminate in the same manner as in Example 5 and the fluorescence image and the intensity distribution were measured. The results are shown in FIGS. 19 and 20. In FIG. 19, the top of the laminate as viewed from the vertical direction is shown at the left of the page. These results confirmed that the percentage depth dose (PDD) of the laminate of the present invention nearly matches the PDD of a standard water phantom.

Example 8

Laminate

Figure 21:
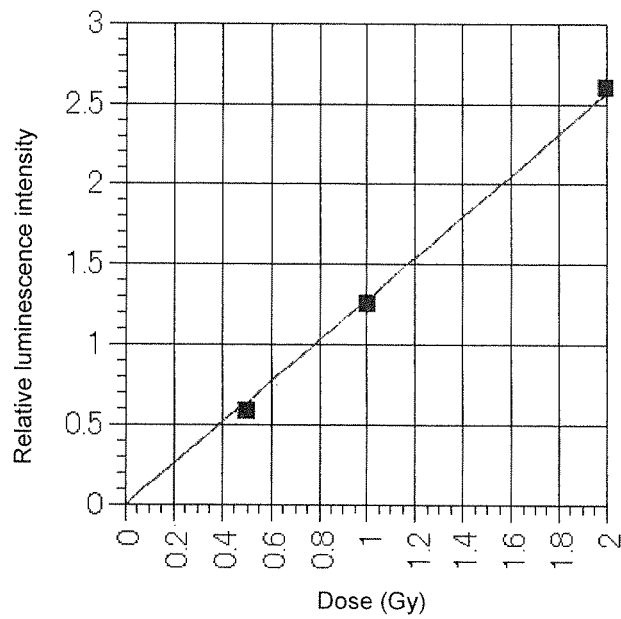
FIG. 21 shows a sensitivity curve of a thin film body versus electron beams.
Figure 22:
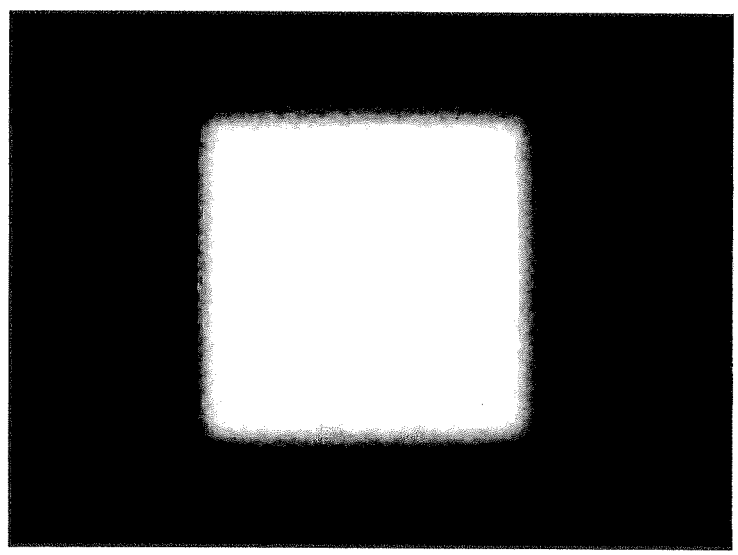
FIG. 22 shows a photoexcited (stimulated) fluorescence image of a thin film body irradiated with electron beams.
Figure 23:
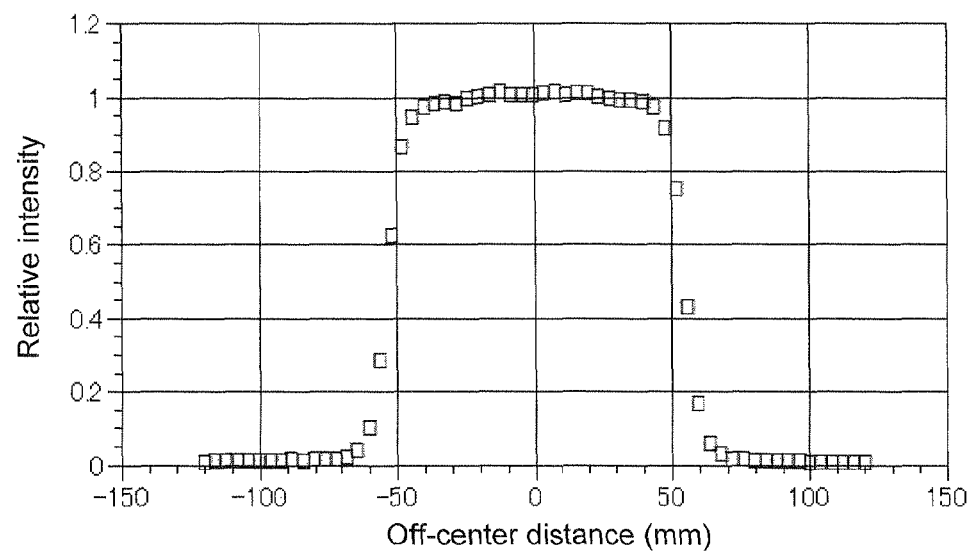
FIG. 23 shows an off-center ratio (versus electron beams).

A laminate obtained in the same manner as in Example 5 was evaluated in the same manner as in Example 5 except that the laminate was irradiated with electron beams (9 MeV) instead of X rays. The results are shown in FIGS. 21 to 23. An almost linear relation was confirmed between the dose and the luminescence intensity. Further, the data of the off-center ratio confirmed that the laminate had sufficient resolution.

Example 9

Laminate

Figure 24:
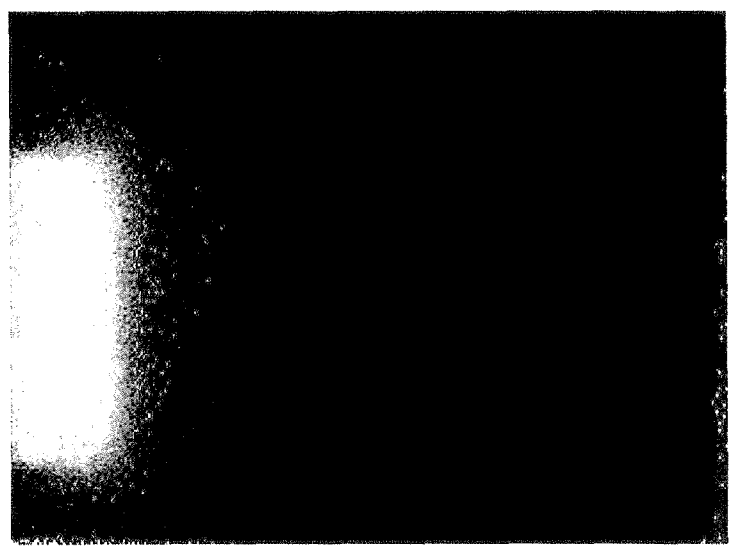
FIG. 24 shows an image of fluorescence photoexcited (stimulated) after irradiation with electron beams.
Figure 25:
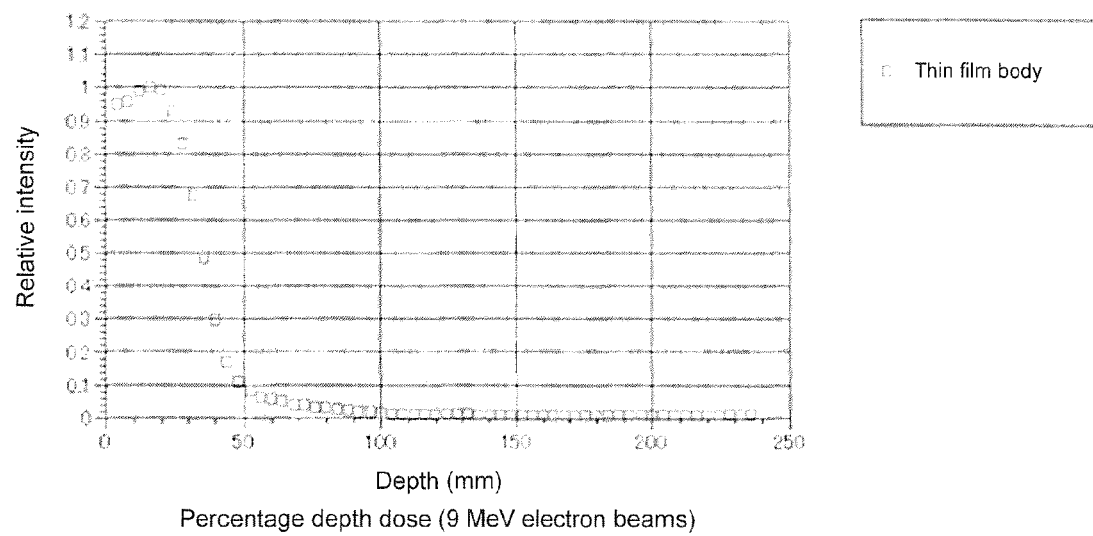
FIG. 25 shows a percentage depth dose of a thin film body.

The laminate was evaluated in the same manner as in Example 7 except that the laminate was irradiated with electron beams (9 MeV) instead of X rays. The results are shown in FIGS. 24 and 25. FIG. 25 shows the percentage depth dose (PDD) of the thin film body; according to the Japan Society of Medical Physics ed., "*Kyushu Senryou no Hyoujun Sokuteihou*" (Standard Method for Absorbed Dose Measurement), pp. 177-183, the PDD of a standard water phantom is shown by almost the same curve as that of FIG. 25. Hence, in the case of electron beams, it could be confirmed that the percentage depth dose (PDD) of the laminate of the present invention also nearly matches the PDD of a water phantom.

Example 10

Laminate

Figure 26:
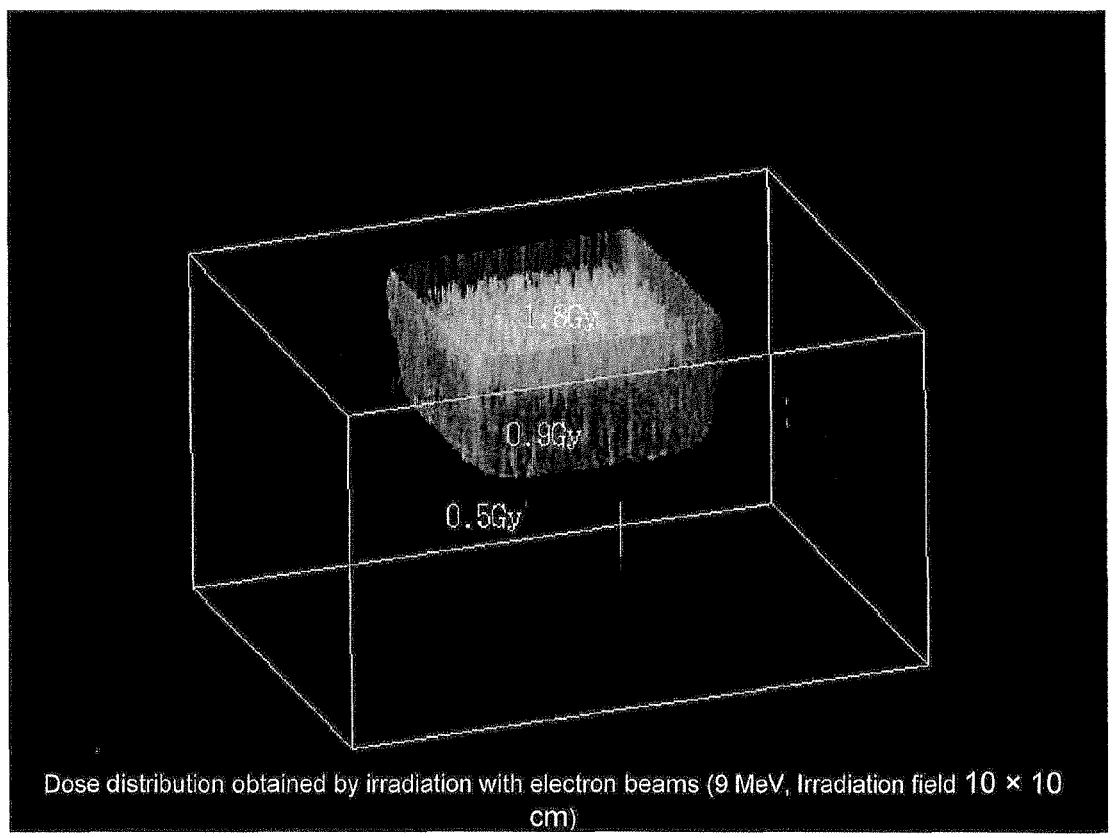
FIG. 26 shows a dose distribution for a laminate of tough water plates and thin film bodies.

A total of 18 thin film bodies obtained in Example 4 (180×240 mm) were sandwiched between two tough water plates to prepare a laminate. The laminate was irradiated with electron beams (9 MeV) from above such that the maximum dose on the tough water plates reached 2 Gy (irradiation field: 10×10 cm). After the irradiation, the laminate was disjointed, the thin film bodies were taken out of the laminate, and the luminescence of each thin film body was imaged and recorded. Each luminescence image was normalized using a standard value and then all the images were assembled to give a three-dimensional dose distribution (FIG. 26). It was confirmed that the laminate of the present invention functions well as a measurement system for a three-dimensional dose distribution even in the case of irradiation with electron beams.

Example 11

Thin Film Body

A urethane gel precursor (trade name: Hapla pudding gel No. 1, which is a product of Polysis Co.) was coated thinly on commonly used tracing paper such that the coating had a thickness of about 0.1 mm. The silver-containing lithium heptaborate powder obtained in Example 1 was sprayed using a sieve (200 mesh: 40 μm opening) and then a pressure was applied to fix the powder in the urethane gel precursor. Thereafter, the precursor was completely cured at room temperature over 5 hours. A thin film body was thus obtained. The mass ratio between the respective components contained in the thin film body was as follows: paper: urethane gel:phosphor=2.09:0.50:1.80 (4.39 g in total). The amount of the silver-containing lithium heptaborate powder contained in the thin film body was 41.0 mass %.

Figure 27:
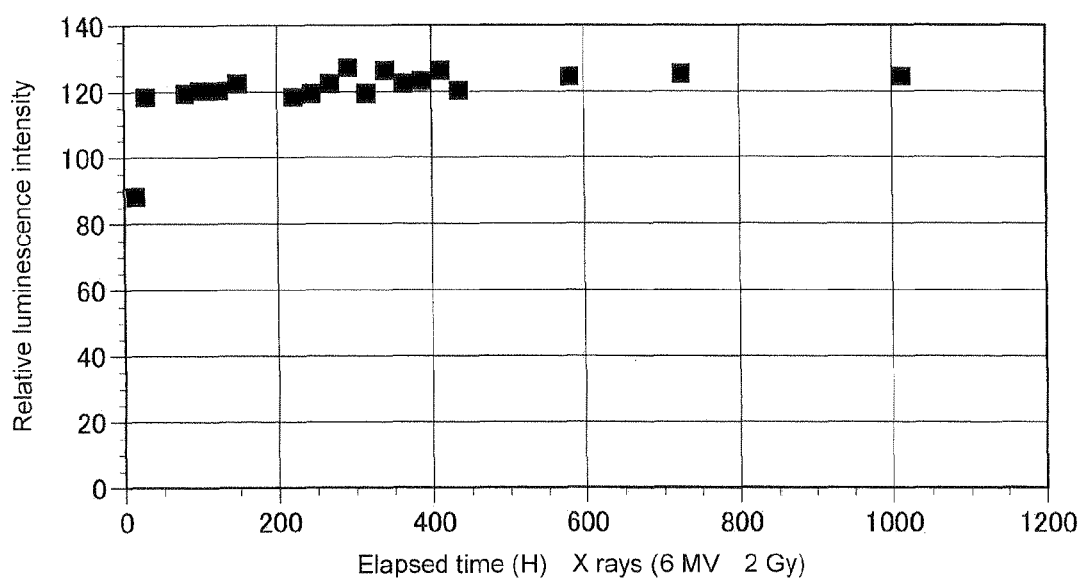
FIG. 27 shows a fading characteristic.

The thin film body was stored in a dark place. After certain periods of time, the luminescence intensity was measured in accordance with Example 1 and the temporal change in luminescence intensity was measured. As a result, no change was observed in the luminescence intensity for a period of 1 month (FIG. 27). FIG. 27 shows the temporal change in luminescence intensity which is based on the initial (0 hour) luminescence intensity taken as 100. FIG. 27 revealed that no fading occurs.

Example 12

Thin Film Body

A sheet whose substrate was coated with acrylic gel in advance (trade name: two-sided adhesive sheet HCP with a thickness of 0.16 mm, which is a product of Horse Care Products Ltd.) was prepared. The silver-containing lithium heptaborate powder obtained in Example 1 was sprayed using a sieve (200 mesh: 40 μm opening) and then a pressure was applied to fix the powder in the acrylic gel. The mass ratio between the respective components contained in the thin film body obtained was as follows: paper: acrylic gel: phosphor=2.30:5.90:1.00 g (9.20 g in total). The thin film body was evaluated in the same manner as in Example 11. As a result, it was revealed that no fading occurs for a period of 1 month.

REFERENCE SIGNS LIST

1 Thin film body
10 Photo stimulable phosphor sheet
20 Paper
30 Biological tissue-equivalent thick plastic plate
100 Cooled CCD camera
102 Ultraviolet camera lens
104 Visible light-cutoff ultraviolet transmission filter
106 Ultraviolet- and heat ray-cutoff plate
108 Blue LED lamp array
110 Door

The invention claimed is:

1. A method for producing a photostimulable phosphor, comprising:
   a step A for mixing lithium tetraborate, boron oxide and silver oxide, and
   a step B for obtaining the photostimulable phosphor comprising lithium heptaborate as a base material and silver as a luminescent center present in the base material by firing the mixture at 820 to 860° C.,
   wherein the molar ratio between the lithium tetraborate and the boron oxide in the step A is X:1, provided that X>1, and the amount of the silver oxide is 0.06 to 1.0 mass % relative to the total mass of the lithium tetraborate and the boron oxide.

2. The method of claim 1, wherein the X is 2 to 4.

3. The method of claim 1, wherein the temperature of the firing is 840 to 860° C. and the time of the firing is 6 hours or more.

4. The method of claim 1, wherein the amount of the silver oxide is 0.06 to 0.08 mass %.

5. A photostimulable phosphor comprising lithium heptaborate as a base material and silver as a luminescent center present in the base material, the photostimulable phosphor having a monomodal luminescence spectrum.

6. The photostimulable phosphor of claim 5 which has a monomodal luminescence spectrum with a maximum value at a range of 300 to 310 nm.

7. A plate comprising the photostimulable phosphor of claim 5.

8. A photostimulable phosphor sheet which comprises the photostimulable phosphor of claim 5 and has a thickness of 0.05 to 1 mm.

9. A thin film body comprising 0.1 to 5 mm-thick paper or biological tissue-equivalent plastic sheet and the photostimulable phosphor sheet of claim 8 which is laminated on the paper or the sheet.

10. A method for producing the thin film body of claim 9, comprising:
    a step C for preparing a powder of the photostimulable phosphor,
    a step D for forming a flowable binder layer on the paper or biological tissue-equivalent plastic sheet,
    a step E for retaining the powder obtained in the step C in the flowable binder layer obtained in the step D by placing the powder on the surface of the flowable binder layer, and
    a step F for solidifying the flowable binder layer.

11. The method of claim 10, wherein the flowable binder in the step D is a thermosetting resin and the thermosetting resin is cured in the step F.

12. A laminate comprising a biological tissue-equivalent plastic plate and the photostimulable phosphor sheet of claim 8 or thin film body of claim 9 which is laminated on the plastic plate.

* * * * *